United States Patent
Doescher

(10) Patent No.: US 8,936,587 B2
(45) Date of Patent: Jan. 20, 2015

(54) FEMININE HYGIENE ABSORBENT DEVICE AND METHOD

(76) Inventor: Deborah Doescher, Edina, MN (US)

( * ) Notice: Subject to any disclaimer, the term of this patent is extended or adjusted under 35 U.S.C. 154(b) by 230 days.

(21) Appl. No.: 13/566,560

(22) Filed: Aug. 3, 2012

(65) Prior Publication Data
US 2014/0039440 A1  Feb. 6, 2014

(51) Int. Cl.
A61F 13/15  (2006.01)

(52) U.S. Cl.
USPC .................................................. 604/385.17

(58) Field of Classification Search
CPC ............... A61F 13/47218; A61F 13/47227; A61F 2013/4729
USPC ........................................ 604/385.17, 385.18
See application file for complete search history.

(56) References Cited

U.S. PATENT DOCUMENTS

| | | | |
|---|---|---|---|
| 4,595,392 A | 6/1986 | Johnson et al. | |
| 5,057,096 A * | 10/1991 | Faglione | 604/385.17 |
| 6,183,456 B1 | 2/2001 | Brown et al. | |
| 6,423,043 B1 * | 7/2002 | Gustafsson | 604/385.01 |
| 6,475,199 B1 | 11/2002 | Gann et al. | |
| 6,676,649 B2 * | 1/2004 | Mizutani | 604/387 |
| 7,806,881 B2 | 10/2010 | Mizutani et al. | |
| 7,927,323 B2 | 4/2011 | Mizutani et al. | |
| 2002/0143309 A1 * | 10/2002 | Glasgow et al. | 604/378 |
| 2005/0004546 A1 * | 1/2005 | Mizutani et al. | 604/385.14 |
| 2005/0010187 A1 | 1/2005 | Mizutani et al. | |
| 2005/0137554 A1 | 6/2005 | Mizutani et al. | |
| 2008/0172018 A1 * | 7/2008 | Chien | 604/385.04 |
| 2009/0266491 A1 | 10/2009 | Mizutani et al. | |
| 2010/0030189 A1 | 2/2010 | Fleming | |
| 2011/0166432 A1 | 7/2011 | Fleming | |

* cited by examiner

Primary Examiner — Lynne Anderson
(74) Attorney, Agent, or Firm — Hinshaw & Culbertson LLP

(57) ABSTRACT

An external absorbent device and a method for absorbing bodily fluids are provided. The external absorbent device includes an external tampon portion movably affixed to a sanitary napkin portion. The external tampon portion can be properly positioned between the labia of the wearer, and the sanitary napkin portion can be affixed to or rest within the crotch portion of an undergarment.

25 Claims, 5 Drawing Sheets

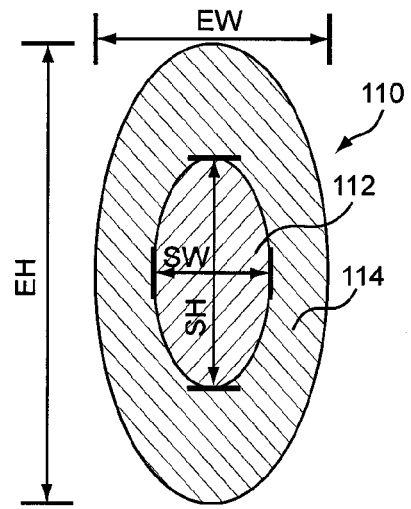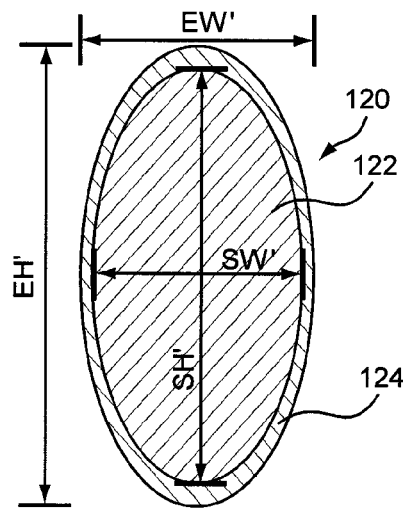
FIG.8A  FIG.8B
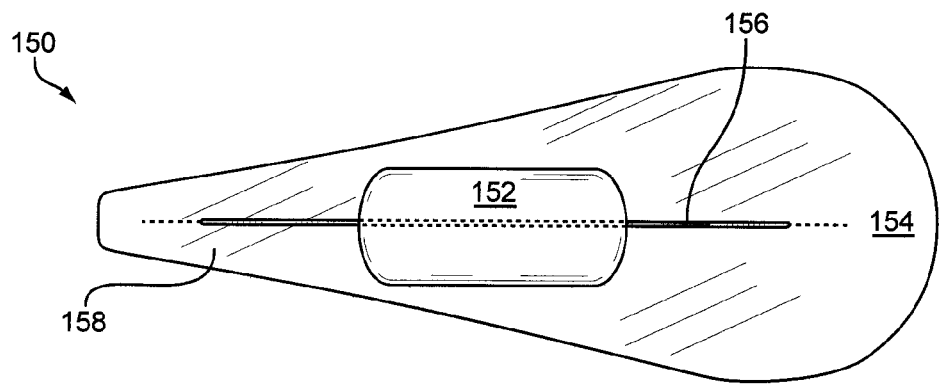
FIG.9
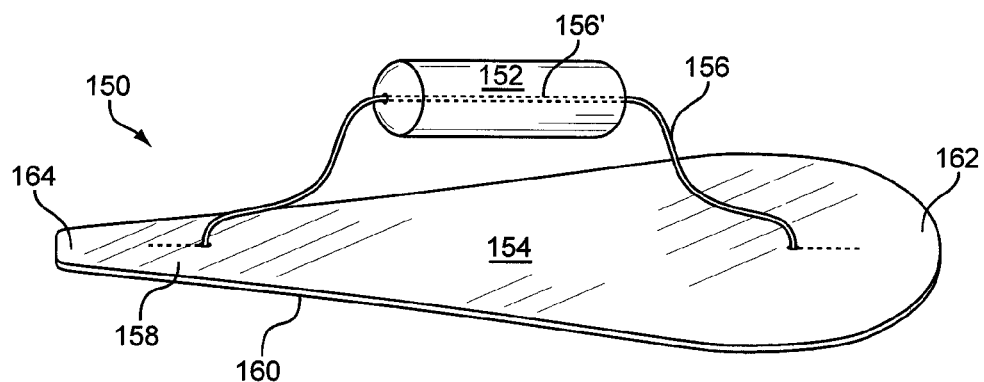
FIG.10

FEMININE HYGIENE ABSORBENT DEVICE AND METHOD

FIELD OF THE INVENTION

The present invention relates to a feminine hygiene absorbent device for absorbing bodily fluids. The present invention also relates to a method for absorbing bodily fluids.

BACKGROUND OF THE INVENTION

A need exists for women to safely, comfortably and discreetly contain bodily fluids such as menses and urine. Conventional tampons are internally inserted into the vaginal cavity and are used to absorb menses. Conventional sanitary napkins or undergarments are worn inside a person's underwear to absorb bodily fluids.

But conventional tampons have drawbacks. During use they are a foreign object inserted into the female body and this inherently can cause various problems, including toxic shock syndrome, a potentially fatal illness. The use of superabsorbent polymers within such tampons increases the risk of toxic shock syndrome and was discontinued from use in the 1980s due to this concern.

Sanitary napkins are not an entirely satisfactory alternative to tampons. Sanitary napkins can be thick and bulky, causing discomfort to the wearer and have limited absorbency where needed. Sanitary napkins can also shift during wear, increasing the risk of embarrassing leaks onto a wearer's clothing.

A need exists for a feminine hygiene absorbent device that decreases the risk of embarrassing leaks and spills of bodily fluids while avoiding the drawbacks of conventional tampons.

BRIEF SUMMARY OF THE INVENTION

In accordance with the present invention, an external feminine hygiene absorbent device is provided. The external absorbent device can be used to absorb bodily fluids and avoids the risks of internally worn tampons. The external absorbent device of the present invention in one embodiment is composed of an external tampon portion and a sanitary napkin portion. The entire external tampon portion is movably secured or affixed to the sanitary napkin portion, to allow movement of the tampon portion relative to the sanitary napkin portion, in at least one dimension, and typically to permit limited three-degree freedom of movement, that is, lateral, longitudinal and vertical movement (movement in three (X, Y and Z) dimensions or coordinates) relative to the external tampon portion relative to the sanitary napkin portion within limits as hereafter described. This arrangement provides the advantages of increased comfort for the user and more reliable interlabial retention of the external tampon portion even during strenuous activities, resulting in better absorption of bodily fluids and improved overall performance of the inventive feminine hygiene device. Thus, where three-degree freedom of movement is provided, the tampon portion can move laterally and longitudinally relative to the sanitary napkin portion, as well as vertically up from resting on the sanitary napkin portion so that the tampon portion can move above the sanitary napkin portion, so that the tampon portion is not in contact with the sanitary napkin portion, and then the tampon portion then can move back down to where it is in contact with the sanitary napkin portion.

The external tampon portion is capable of absorbing fluids. Typically, the external tampon portion is composed of absorbent material or materials. The tampon portion has an outer surface for coming into contact with a woman's labia and can be configured for being positioned interlabially or at least partially interlabially in the form of an elongated body of any suitable material or materials. In one embodiment the tampon body has first and second ends that may be generally rod-shaped and has an outer surface suitable for contacting a labia. Typically, in use, the external tampon portion is at least partially positioned interlabially of a user.

The sanitary napkin portion in accordance with the invention also absorbs fluids, thereby increasing the overall capacity of the feminine hygiene device and can be composed of any suitable material. As used herein, the "entire tampon portion" excludes strings or mounting devices. The sanitary napkin portion is typically an elongated member having a first end, a second end, a first side, a second side, a top surface, and a bottom surface. The bottom surface typically contains an adhesive to attach the sanitary napkin portion to the crotch portion of an undergarment.

The external tampon portion of the inventive feminine hygiene device is movably affixed to the sanitary napkin portion in any suitable manner that allows for limited movement in at least one dimension, and typically to permit lateral, longitudinal and vertical movement of the tampon portion relative to the sanitary napkin portion. Typically, the external tampon portion is affixed to the sanitary napkin portion by one or more relatively thin, flexible and non-rigid elongated members, which may be, for example, strings, threads or bands of suitable material. More specifically, in one embodiment, the external tampon portion is affixed to the sanitary napkin portion by one or more and typically up to four strings. The strings have sufficient length or slack between the napkin and tampon portions to permit a desired range of three-dimensional movement, e.g., lateral, longitudinal and vertical movement of the tampon portion relative to the napkin portion. The flexible and non-rigid elongated member may be elastic (i.e., stretchable like a rubber band or elastic cord, or inelastic or relatively inelastic, as a conventional cotton thread or string, for example. Elastic elongated attaching members can be used with little or no slack if desired to keep the tampon portion in a desired home position, i.e., in contact with and located as desired on the sanitary napkin portion, while still allowing the three-dimensional movement as described herein.

In one embodiment, the external tampon portion is a mass of fibers, which may be a compressed body of fibers. The external tampon portion can include superabsorbent material, typically contained within the interior of the tampon portion. In one aspect of the invention, the external tampon portion is pliable. In use, the external tampon portion of the device can be fitted between the user's two labia.

In one aspect of the invention, the sanitary napkin portion includes a plurality of absorbent layers. At least one of the layers can include a superabsorbent material.

In one embodiment, the sanitary napkin portion includes a topsheet and an absorbent core. The absorbent core can include a fibrous web that can absorb fluids. In a particular embodiment, the bottom side of the sanitary napkin portion includes an adhesive material. The adhesive material allows the sanitary napkin to be affixed to the crotch portion of an undergarment.

In another embodiment, the external absorbent device includes a first string having first and second ends, a second string having first and second ends, a third string having first and second ends, and a fourth string having first and second ends, in which the four strings affix the external tampon to the sanitary napkin, with sufficient slack to permit the desired permitted extent of three-dimensional movement, i.e., lateral, longitudinal and vertical movement, of the external tampon portion relative to the sanitary napkin portion. In another aspect of the invention, the first end of the first string is connected to the first end of the external tampon and the second end of the first string is connected to a first side of the sanitary napkin, the first end of the second string is connected to the first end of the external tampon and the second end of the second string is connected to the second side of the sanitary napkin, the first end of the third string is connected to the second end of the external tampon and the second end of the third string is connected to the first side of the sanitary napkin, and the first end of the fourth string is connected to the second end of the external tampon and the second end of the fourth string is connected to the second side of the sanitary napkin, each of the four strings having sufficient slack to permit back and forth lateral and longitudinal movement and up and down vertical movement. In a more specific embodiment of the invention, the first string and the second string are about the same length, and the third string and the fourth string are about the same length. In still a more specific aspect of the invention, the first string, the second string, the third string, and the fourth string are about the same length. In a normal or "home" position, the tampon portion rests on the surface of the sanitary napkin portion of the absorbent device, typically centrally located in the sanitary napkin portion.

In one embodiment, during use the external tampon portion is movably positionable between the user's two labia.

In another embodiment, a method of absorbing bodily fluids is provided. One of the external absorbent devices as previously described is provided. In use, the device is attached to an undergarment by attaching the sanitary napkin portion of the device to the crotch portion of an undergarment so that during normal wearing and use of the undergarment, the external tampon portion is interlabially positioned on the wearer.

In another embodiment, the positioning of the external tampon portion is adjusted relative to the wearer's body to ensure a comfortable fit.

In another embodiment, the external absorbent device can include a first string, a second string, a third string, and a fourth string, wherein the four strings attach the external tampon portion to the sanitary napkin portion, and wherein the four strings are about the same length.

In one embodiment of the invention, the external tampon portion is a mass of compressed fibers and superabsorbent material, and the sanitary napkin portion includes a topsheet and an absorbent core. The absorbent core comprises a fibrous web that can absorb fluids. Optionally, a superabsorbent material can be included in the absorbent core of the sanitary napkin portion.

In a further embodiment of the invention, after the external tampon portion is interlabially positioned, fluids are absorbed in the external tampon portion, and any spillover fluids are absorbed in the sanitary napkin portion.

BRIEF DESCRIPTION OF THE DRAWINGS

FIG. 8A is a cross sectional view of another embodiment of an external tampon portion in accordance with the present invention.

FIG. 8B is a cross sectional view of another embodiment of an external tampon portion in accordance with the present invention.

FIG. 9 is a top plan view of an alternate embodiment external absorbent device in accordance with the invention.

FIG. 10 is a perspective view of the device of FIG. 9.

DETAILED DESCRIPTION OF THE INVENTION

Figure 1:
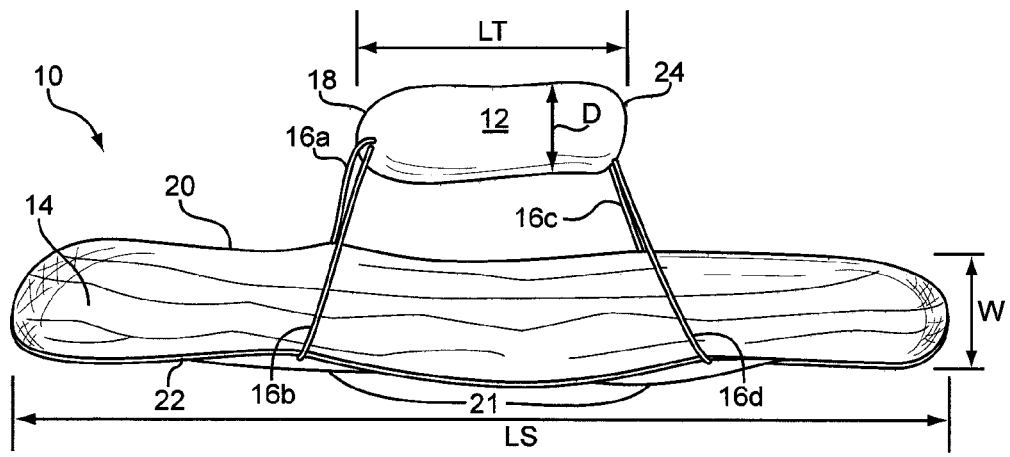
FIG. 1 is a perspective view of an external absorbent device in accordance with the present invention.

The present invention is directed to a feminine hygiene external absorbent device. The external absorbent device can be used to absorb bodily fluids such as urine, menses, or fecal matter. The external absorbent device is used externally to the body and provides a discreet way to comfortably, cleanly, and efficiently absorb bodily fluids in a healthy manner, without the risks associated with internal tampons.

The external absorbent device includes an external tampon portion that is movably attached to a sanitary napkin portion, permitting limited three-dimensional movement (i.e., lateral, longitudinal and vertical movement), relative to the sanitary napkin portion. The external tampon portion can be movably attached to the sanitary napkin portion using any appropriate attachment mechanism. Typically, the external tampon portion is movably affixed to the sanitary napkin portion using one or more elongated elastic or inelastic attaching members, which may be, for example, strings, threads or bands or other members with sufficient slack in the strings or threads so that lateral, transverse and vertical movement of the tampon portion is permitted within the limits of the slack or elasticity of the attaching members relative to the sanitary napkin portion. In various embodiments, the external tampon portion is movably attached to the sanitary napkin portion using from one to four strings.

In one embodiment, the external tampon portion is generally rod-shaped. Typically, the external tampon portion has a longitudinal axis, which refers to the longest linear dimension of the external tampon portion. In one embodiment, the external tampon portion is between about 2.5 centimeters and about 6.5 centimeters long along the longitudinal axis. Typically, the external tampon portion is between about 3 centimeters and about 5 centimeters long along the longitudinal axis. Most typically, the external tampon portion is between about 3.5 centimeters and about 4 centimeters long along the longitudinal axis.

The external tampon portion can be a generally oblong pillow-shaped body. The pillow-shaped body conforms to the shape and fit of a female wearer's labia. The pillow is flexible and moldable to the female wearer's labia. This allows the external tampon portion to absorb a maximum amount of fluid while still maintaining the comfort of the wearer.

The cross-section of the external tampon portion can be any desired or suitable shape and can vary along its length or be of a uniform cross-sectional shape. A cylindrical or generally oval cross-sectional shape is one common shape of many that can be used. The cross-section is a slice taken at a right angle to the longitudinal axis. In one embodiment, the external tampon portion has a generally cylindrical cross-section. The generally cylindrical cross-section can be the usual shape of conventional internal tampons as is well known in the art, and also includes oblate or partially flattened cylinders, curved cylinders, and shapes which have varying cross-sectional areas. The external tampon portion typically has a large diameter of between about 0.75 centimeters and about 1.75 centimeters. More typically, the external tampon portion has a large diameter of between about 1 centimeter and about 1.5 centimeters. Most typically, the external tampon portion has a large diameter of between about 1.2 centimeters and about 1.4 centimeters. The external tampon portion typically has a small diameter of between about 0.75 centimeters and about 1.75 centimeters. More typically, the external tampon portion has a small diameter of between about 1 centimeter and about 1.5 centimeters. Most typically, the external tampon portion has a small diameter of between about 1.2 centimeters and about 1.4 centimeters. When the external tampon portion has a generally circular cross-section, the large diameter and small diameter are about the same.

The strings that attach the external tampon portion to the sanitary napkin portion allow movement of the external tampon portion in relation to the sanitary napkin portion, laterally, longitudinally and vertically. This assures an individual fit for each female wearer. The amount that the external tampon portion can move in relation to the sanitary napkin portion depends on the length of the strings. In one embodiment, the external tampon portion can move longitudinally and be positioned along about 90% of the length of the sanitary napkin portion. Typically, the external tampon portion can move longitudinally between about 10% and about 90% of the length of the sanitary napkin portion. More typically, the external tampon portion can move between about 50% and about 85% of the length of the sanitary napkin portion. Typically, the external tampon portion can be positioned along any suitable point of the width of the sanitary napkin portion. More typically, the external tampon portion can move laterally between about 70% and about 95% of the width of the sanitary napkin portion. Vertical movement is also permitted, and typically the external tampon portion can move vertically about 0.5 to about 5 centimeters directly above the napkin portion, and more typically from about 1 to about 5 centimeters above the napkin portion.

In one embodiment, each of the four strings that attach the external tampon portion to the sanitary napkin portion is typically about the same length. The strings that attach the external tampon portion to the sanitary napkin portion are typically between about 2 centimeters and about 6 centimeters long. More typically, the strings are between about 3 centimeters and about 5 centimeters long. Most typically, the strings are between about 3.5 centimeters and about 4.5 centimeters long.

The external tampon portion is typically longitudinally positioned in about the middle of the length of the sanitary napkin portion. Typically, the external tampon portion is approximately centered over the sanitary napkin portion. The strings allow the external tampon portion to move in relation to the sanitary napkin portion. Typically, the external tampon portion can move between about 1 centimeters and about 5 centimeters forward and between about 1 centimeters and about 5 centimeters backwards from the center of the sanitary napkin portion, along the length of the sanitary napkin portion. More typically, the external tampon portion can move between about 2 centimeters and about 4 centimeters forward and between about 2 centimeters and about 4 centimeters backwards from the center of the sanitary napkin portion, along the length of the sanitary napkin portion.

The external tampon portion may be constructed of any suitable material, and typically comprises a mass of compressed fibers. The compressed fibers can include any absorbent material or a combination or blend of absorbent and non-absorbent material. Typically, the external tampon portion comprises material selected from cotton, rayon, polymers, superabsorbent polymers, absorbent gelling and open-celled foams, or any combination thereof.

Suitable superabsorbent polymers can be selected from polymers that can absorb and retain extremely large amounts of liquid relative to their own mass. Superabsorbent polymers include any polymer that comprises water-swellable, water-insoluble organic or inorganic materials capable of absorbing at least about 20 times their weight in an aqueous solution containing 0.9 weight percent of sodium chloride. The superabsorbent polymers absorb aqueous solutions through hydrogen bonding with water molecules. Organic materials suitable for use as a superabsorbent material can be selected from natural materials such as polysaccharides, polypeptides and the like, as well as synthetic materials such as synthetic hydrogel polymers. Typically, the superabsorbent polymer is made from the polymerization of acrylic blended with sodium hydroxide in the presence of an initiator to form sodium polyacrylate. Other superabsorbent polymers can be selected from polymers such as a polyacrylamide copolymer, ethylene maleic anhydride copolymer, cross-line carboxymethylcellulose, polyvinyl alcohol copolymers, polyvinyl pyridines, cross-linked polyethylene oxide, starch grafted copolymer of polyacrylonitrile, acrylic acid grafted starch, isobutylene maleic anhydride copolymers and mixtures thereof. The hydrogel polymers are preferably lightly cross-linked to render the material substantially water insoluble.

Typically, the superabsorbent materials are further surface cross-linked so that the outer surface or shell of the superabsorbent particle, fiber, flake, sphere, etc. possesses a higher crosslink density than the inner portion of the superabsorbent material. The superabsorbent materials may be in any form suitable for use in absorbent composites including particles, fibers, flakes, spheres, and the like.

The external tampon portion may comprise a plurality of layers. In one embodiment, the external tampon portion comprises an absorbent material layer and an overwrap layer.

The absorbent material layer can be comprised of any absorbent material or a combination or blend of absorbent and non-absorbent material. In one embodiment, the external tampon portion comprises cotton, rayon, polymers, superabsorbent polymers, or any combination thereof. The absorbent material layer may be a laminar structure comprised of integral or discrete layers. In other embodiments, the absorbent material layer need not have a layered structure.

The external tampon portion is typically a pliable material of a size so that at least a portion of which can be fitted in between two labia. The external tampon portion will rest in place between the two labia without entering the body or vaginal cavity.

The sanitary napkin portion can have a longitudinal axis, which refers to the longest linear dimension of the sanitary napkin portion. The sanitary napkin portion is between about 10 centimeters and about 25 centimeters long typically along its longitudinal axis. Typically, the sanitary napkin portion is between about 12 centimeters and about 20 centimeters long along its longitudinal axis. Most typically, the sanitary napkin portion is between about 14 centimeters and about 18 centimeters long typically along its longitudinal axis.

The sanitary napkin portion typically has a horizontal axis, which refers to the shortest linear dimension of the sanitary napkin portion. The sanitary napkin portion can be of a size and shape as desired. Typically, the sanitary napkin portion is between about 3 centimeters and about 8 centimeters wide along its horizontal axis. More typically, the sanitary napkin portion is between about 4 centimeters and about 7 centimeters wide typically along its horizontal axis, and the sanitary napkin portion is between about 4.5 centimeters and about 6 centimeters wide along its horizontal axis.

In one embodiment, the sanitary napkin is a thong panty liner. The thong panty liner in accordance with the invention is of a size and shape to permit it to be contained within a thong panty or a thong bathing suit. Consequently, typically the thong panty liner is wider at one end (front) and gradually tapers to a narrower end (rear), allowing it to be placed on a thong panty or bathing suit and contained therein so that it is not exteriorly visible. While the thong panty liner of the invention can be of a size and shape as desired, typically, the thong panty liner is between about 12 centimeters and about 20 centimeters long along its longitudinal axis. Most typically, the thong panty liner is between about 14 centimeters and about 18 centimeters long typically along its longitudinal axis. The thong panty liner is typically between about 3 centimeters and about 8 centimeters wide at the first end (front), and is typically between about 0.25 centimeters and about 3 centimeters at the second end (rear). More typically, the thong panty liner is between about 4 centimeters and about 7 centimeters at the first end, and is typically between about 0.5 centimeters and about 2 centimeters at the second end.

In one embodiment, the sanitary napkin portion contains a compressed mixed or layered structure of cellulosic fluff pulp and superabsorbent polymers. The sanitary napkin portion can be a multilayer sanitary napkin portion. The different layers of the sanitary napkin portion can comprise different materials with different properties with respect to fluid receiving capacity, fluid distribution capacity and fluid storage capacity. A high absorption capacity is provided by the use of high amounts of superabsorbent polymers.

The sanitary napkin portion of the device may comprise an absorbent core and an overwrap layer. The absorbent core can comprise a fibrous web that can absorb fluids. For an absorbent core comprising a matrix of hydrophilic fibers, such as cellulosic fibers, and superabsorbent material, the proportion of superabsorbent material is typically between 10% and 90% by weight, more preferably between 30% and 70% by weight. The absorbent core may also include laminates of roll materials, such as airlaid tissue, nonwovens and through-air-dried tissue, and superabsorbent materials, wherein an inner layer or strings of superabsorbent material is present between outer layers of said roll material. The different layers of such a laminate are bonded together by, for example, glue or by heat bonding.

The external absorbent device is described in more detail with reference to the accompanying figures.

Figure 2:
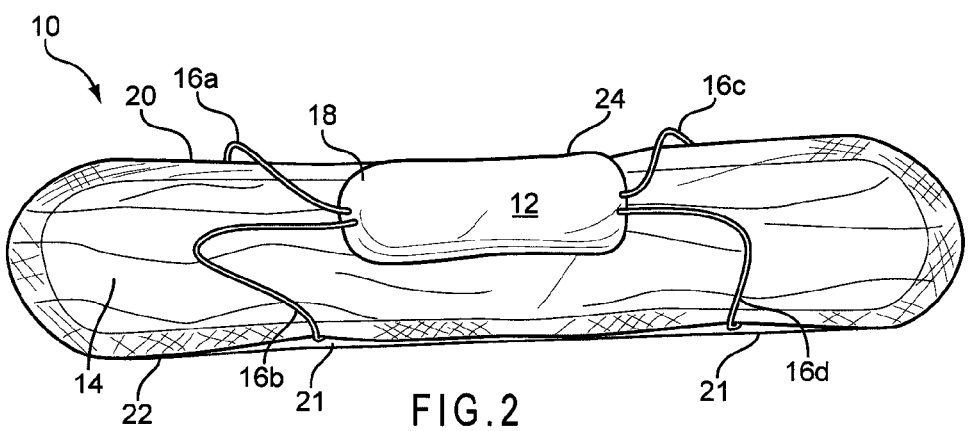
FIG. 2 is a perspective view of the external absorbent device of FIG. 1, showing the tampon portion in the normal or home position resting on the napkin portion.

For illustrative purposes, tampon portion 12 is shown vertically raised above sanitary napkin portion 14, although it is to be understood that the normal resting or home position for tampon portion 12 would be in contact with the surface of sanitary napkin portion 14 and typically generally centrally located thereon, as shown in FIG. 2. Obviously, gravity would cause tampon portion 12 to rest on the surface of sanitary napkin portion 14 as shown in FIG. 2, as strings 16a-d do not have stiffness to elevate tampon portion 12, and movement of tampon portion 12 laterally and longitudinally is permitted when resting on sanitary napkin portion 14.

Figure 5:
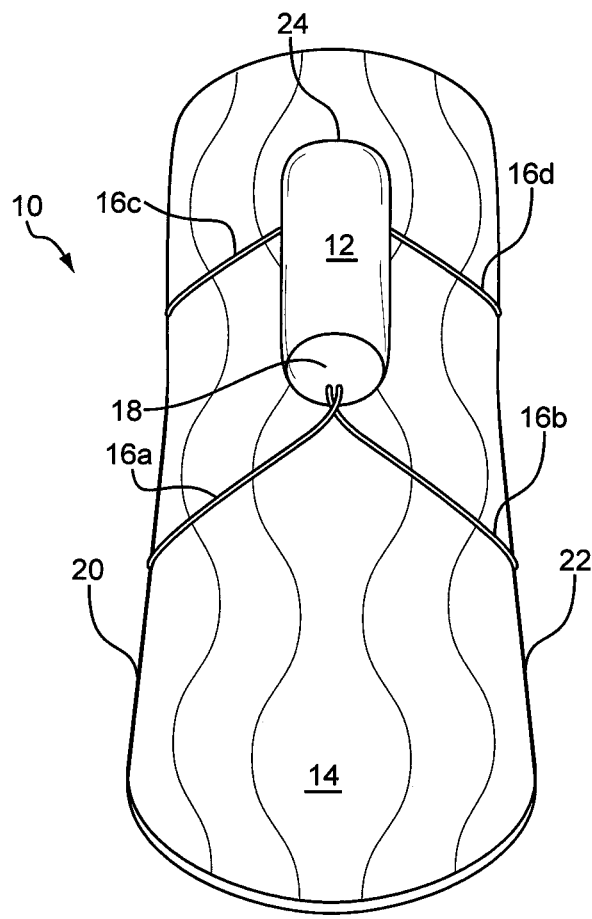
FIG. 5 is a perspective view of the external absorbent device of FIG. 1.

An external absorbent device 10 in accordance with the invention is generally illustrated in FIGS. 1, 2, and 5. External absorbent device 10 comprises an external tampon portion 12 and a sanitary napkin portion 14. External tampon portion 12 is movably affixed to sanitary napkin portion 14 via strings 16a-d, allowing lateral, longitudinal and vertical movement relative to sanitary napkin portion 14. First string 16a is attached within a first end 18 of external tampon portion 12 and at a first side 20 of sanitary napkin portion 14. Second string 16b is attached within a first end 18 of external tampon portion 12 and at a second side 22 of sanitary napkin portion 14. Third string 16c is attached within a second end 24 of external tampon portion 12 and to first side 20 of sanitary napkin portion 14. Fourth string 16d is attached within second end 24 of external tampon portion 12 and to second side 22 of sanitary napkin portion 14. Strings 16a-d may be secured to tampon portion 12 and napkin portion 14. In the illustrated embodiment of FIG. 1, strings 16a-d are compressively held within tampon portion 12 and adhesively secured between the bottom of first side 20 and outer layer 21 of napkin portion 14. Alternatively, as a non-limiting example, strings 16a-d could be sewn or knotted to tampon portion 12 and napkin portion 14, or attached in any other suitable manner. For example, the string end could incorporate a plastic (or material) barb to ensure that the string end is retained in tampon portion 12. Also, strings 16a,b may be a single string, the two ends of which are secured to sanitary napkin portion 14 as shown in FIG. 1, and a similar single string arrangement may be used in place of strings 16c,d. Strings 16a-d movably secure external tampon portion 12 to sanitary napkin portion 14, allowing external tampon portion 12 to move with respect to sanitary napkin portion 14 to a degree limited by the slack of strings 16a-d. But while the tampon portion 12 is permitted limited relative movement, end-over-end rotation of tampon portion 12 relative to sanitary napkin portion 14 is not permitted, as will be appreciated by one skilled in the art. Similarly, the slack of strings 16a-d or their elasticity (and slack if present) in the case of elastic members, will typically be such that movement of the sides of sanitary napkin portion 14 will be prevented. Thus, during normal wearing of absorbent device 10 tampon portion 12 would not move outside of sanitary napkin portion 14 and thus would not be exteriorly visible. External tampon portion 12 can move laterally, longitudinally, or vertically with respect to sanitary napkin portion 14. This allows for a secure fit of external tampon portion 12 between the labia of a wearer, especially during movement by the wearer of device 10 and/or by the sanitary napkin portion 14. External tampon portion 12 is movably positionable between the labia of a wearer, ensuring a snug and body conforming fit. FIG. 2 shows tampon portion 12 in the "home" or normal position, resting on the surface and centrally located on sanitary napkin 14, with strings 16a-d exhibiting slack that permits a desired amount of three-dimensional or X, Y and Z coordinate movement (i.e., lateral, transverse and vertical) of tampon portion 12 relative to sanitary napkin portion 14.

External tampon portion 12 has a length LT along the longitudinal axis. Typically, length LT is between about 2.5 centimeters and about 6.5 centimeters. Typically, external tampon portion 12 has a diameter D. Diameter D is between about 0.75 centimeters and about 1.75 centimeters.

Sanitary napkin portion 14 has a length LS as desired typically along its longitudinal axis. Typically, length LS is between about 3 centimeters and about 8 centimeters, with the ends and/or sides curved or otherwise shaped, as desired. Sanitary napkin portion 14 has a width W typically along its horizontal axis. Typically, width W is between about 4 centimeters and about 7 centimeters, again, with the ends and/or sides curved or otherwise shaped, as desired.

Figure 3:
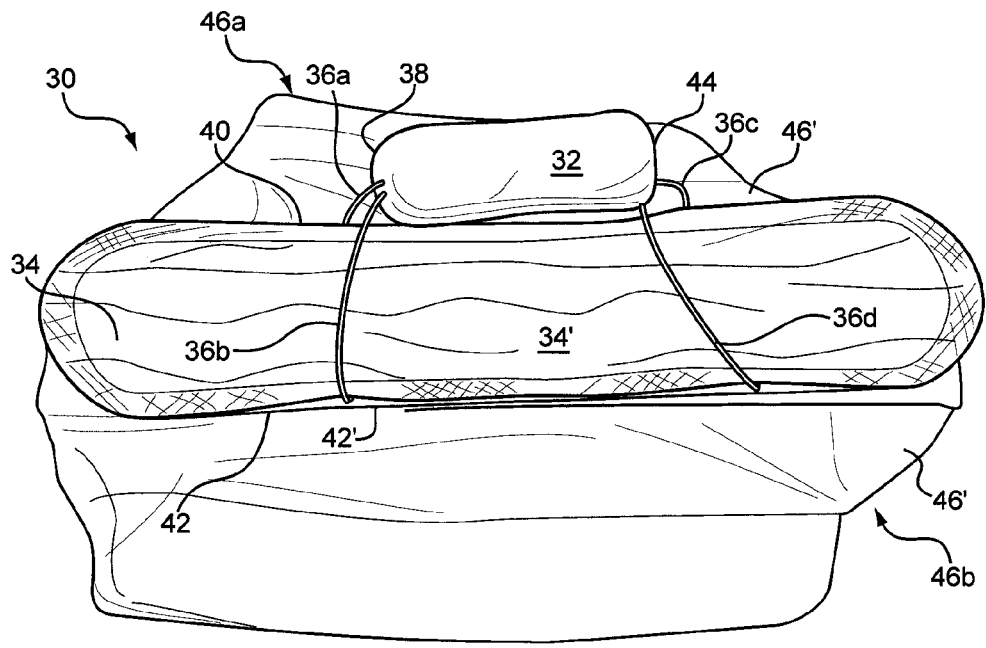
FIG. 3 is a perspective view of another embodiment of an external absorbent device in accordance with the present invention.
Figure 6:
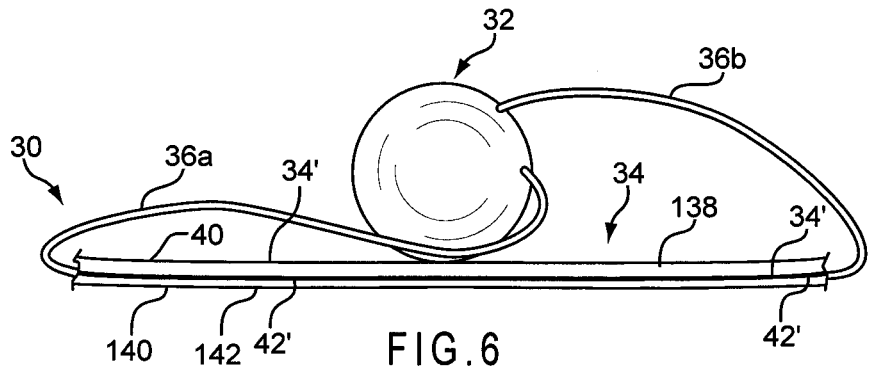
FIG. 6 is a front elevation view of the external absorbent device of FIG. 3, showing the tampon portion in the home position.

In another embodiment, an external absorbent device 30 in accordance with the invention is illustrated in FIGS. 3 and 6. External absorbent device 30 comprises an external tampon portion 32 and a sanitary napkin portion 34. External tampon portion 32 is movably affixed to sanitary napkin portion 34 via strings 36$a$-$d$. First string 36$a$ is attached to a first end 38 of external tampon portion 32 and at a first side 40 of sanitary napkin portion 34. Second string 36$b$ is attached to first end 38 of external tampon portion 32 and at a second side 42 of sanitary napkin portion 34. Third string 36$c$ is attached to a second end 44 of external tampon portion 32 and to first side 40 of sanitary napkin portion 34. Fourth string 36$d$ is attached to second end 44 of external tampon portion 32 and to second side 42 of sanitary napkin portion 34. Strings 36$a$-$d$ movably affix external tampon portion 32 to sanitary napkin portion 34, allowing external tampon portion 32 to freely move with respect to sanitary napkin portion 34. Also, strings 36$a,b$ may be a single string, the two ends of which are secured to sanitary napkin portion 34 as shown in FIG. 3, and a similar single string arrangement may be used in place of strings 36$c,d$. External tampon portion 32 can move laterally, horizontally, or vertically with respect to sanitary napkin portion 34. This allows for a secure fit of external tampon portion 32 between the labia of a wearer. External tampon portion 32 is movably positionable between the labia of a wearer, ensuring a snug and body conforming fit.

Sanitary napkin portion 34 comprises sanitary wings 46$a$-$b$. Sanitary wings 46$a$-$b$ allow sanitary napkin portion 34 to be more securely affixed to an undergarment, wrapping around the crotch portion of an undergarment, thus reducing movement of sanitary napkin portion 34. Alternatively, wings 46$a$-$b$ may have an adhesive layer, which may be adhesive tape, suitably located to secure wings 46$a$-$b$ to an undergarment. Sanitary wings 46$a$-$b$ comprise an absorbent material 46' and extend laterally from first longitudinal side 40 of sanitary napkin portion 34 and from second longitudinal side 42 of sanitary napkin portion 34.

Figure 4A:
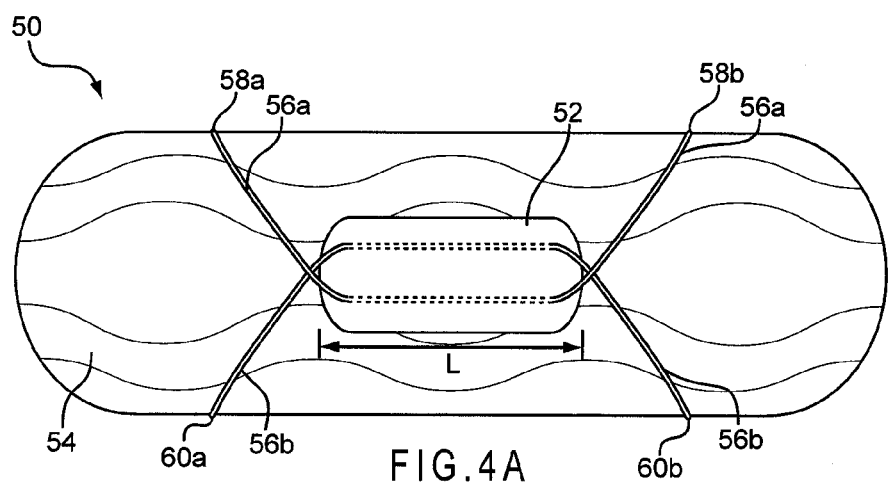
FIG. 4A is a top plan view of an alternative embodiment external absorbent device in accordance with the present invention.

In another embodiment as illustrated in FIG. 4A, external absorbent device 50 comprises an external tampon portion 52 and a sanitary napkin portion 54. External tampon portion 52 is connected to sanitary napkin portion 54 by strings 56$a$-$b$. String 56$a$ passes through length L of external tampon portion 52 and connects to sanitary napkin portion 54 at an attachment point 58$a$ and an attachment point 58$b$. String 56$b$ passes through length L of external tampon portion 52 and connects to sanitary napkin portion 54 at an attachment point 60$a$ and an attachment point 60$b$. Attachment point 58$a$ is on the same side of sanitary napkin portion 54 as attachment point 58$b$. Attachment point 60$a$ is on the same side of sanitary napkin portion 54 as attachment point 60$b$. Attachment points 58$a$-$b$ are on opposite sides of sanitary napkin portion 54 as attachment points 60$a$-$b$.

Figure 4B:
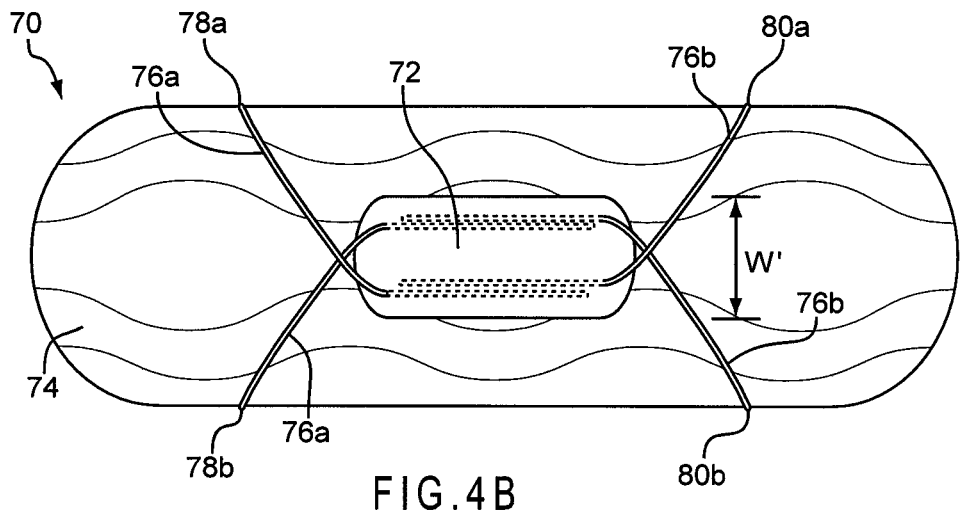
FIG. 4B is a top plan view of another embodiment of an external absorbent device in accordance with the present invention.

In another embodiment as illustrated in FIG. 4B, external absorbent device 70 comprises an external tampon 72 and a sanitary napkin 74. External tampon 72 is connected to sanitary napkin 74 by strings 76$a$-$b$. String 76$a$ passes through width W' of external tampon 72 and connects to sanitary napkin 74 at an attachment point 78$a$ and an attachment point 78$b$. String 76$b$ passes through the width W' of external tampon 72 and connects to sanitary napkin 74 at an attachment point 80$a$ and an attachment point 80$b$. Attachment point 78$a$ is on the opposite side of sanitary napkin 74 as attachment point 78$b$. Attachment point 80$a$ is on the opposite side of sanitary napkin 74 as attachment point 80$b$. Attachment point 78$a$ is on the same side of sanitary napkin 74 as attachment point 80$a$. Attachment point 78$b$ is on the same side of sanitary napkin 74 as attachment point 80$b$.

External tampons can comprise many different shapes and sizes. External tampons can be generally circular, generally oval, a generally oblong pillow-shape, or a generally rectangular pillow-shape. The external tampon has a height and a width. The width can be between about 10% and about 100% of the height. Typically, the width is between about 40% and about 100% of the height. External tampons can comprise different layers, including a superabsorbent core and an outer layer. Typically, external tampons include at least a superabsorbent core and an outer layer. The superabsorbent core comprises superabsorbent material. External tampons can include additional layers as well, each layer comprising different absorbent materials. In the case where the external tampon has a superabsorbent core and an outer layer, the superabsorbent core can be any percentage of the external tampon. Typically, the superabsorbent core has a diameter that is between about 10% and about 95% of the diameter of the external tampon. More typically, the superabsorbent core has a diameter that is between about 25% and about 75% of the diameter of the external tampon.

Figure 7A:
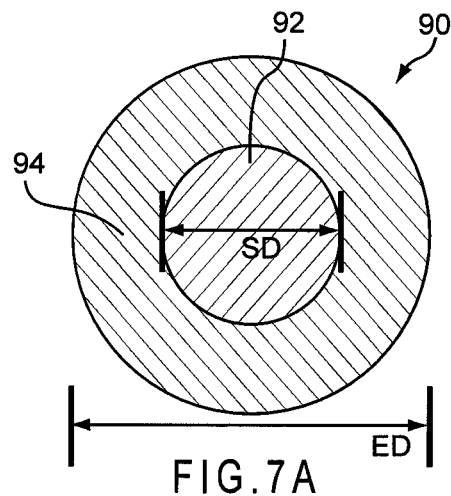
FIG. 7A is a cross sectional view of an external tampon portion in accordance with the present invention.

In one embodiment, as illustrated in FIG. 7A, external tampon 90 is generally circular. External tampon 90 comprises a superabsorbent core 92 and an outer layer 94. Superabsorbent core 92 can be any proportion of external tampon 90. Superabsorbent core 92 has a diameter SD and external tampon 90 has a diameter ED. Diameter SD is about 50% of diameter ED.

Figure 7B:
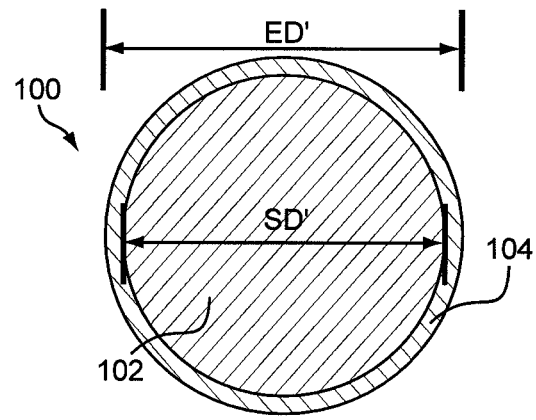
FIG. 7B is a cross sectional view of another embodiment of an external tampon portion in accordance with the present invention.

In another embodiment, as illustrated in FIG. 7B, external tampon 100 is generally circular. External tampon 100 comprises a superabsorbent core 102 and an outer layer 104. Superabsorbent core 102 can be any proportion of external tampon 100. Superabsorbent core 102 has a diameter SD' and external tampon 100 has a diameter ED'. Diameter SD' is about 90% of diameter ED'.

Alternatively, in another embodiment as illustrated in FIG. 8A, external tampon 110 is generally an oblong pillow-shape. External tampon 110 comprises a superabsorbent core 112 and an outer layer 114. External tampon 110 has a height EH and a width EW. Width EW is about 50% of height EH. Superabsorbent core 112 has a width SW and a height SH. Width SW of superabsorbent core 112 is about 50% of width EW of external tampon 110. Height SH of superabsorbent core 112 is about 50% of height EH of external tampon 110.

As illustrated in FIG. 8B, external tampon 120 is generally an oblong pillow-shape. External tampon 120 comprises a superabsorbent core 122 and an outer layer 124. External tampon 120 has a height EH' and a width EW'. Width EW' is about 50% of height EH'. Superabsorbent core 122 has a width SW' and a height SH'. Width SW' of superabsorbent core 122 is about 90% of width EW' of external tampon 120. Height SH' of superabsorbent core 122 is about 90% of height EH' of external tampon portion 120.

The sanitary napkin portion can comprise a plurality of layers. Each layer can include different or the same absorbent materials and wicking materials as other layers. Typically, the sanitary napkin portion includes at least two layers, a wicking layer and a superabsorbent layer. The wicking layer wicks bodily fluids away from the wearer's body. The superabsorbent layer includes absorbent materials that absorb any bodily fluids to prevent leaks and spills onto the wearer's undergarment. The sanitary napkin portion can also include a third, non-permeable layer. The non-permeable layer serves as a barrier between the other layers of the sanitary napkin and the wearer's undergarment, preventing bodily fluids from passing through the superabsorbent layer and onto the wearer's undergarment. Typically, the wicking layer is about the same height as the superabsorbent layer, and the non-permeable layer has a height about 50% of the superabsorbent layer and the wicking layer.

As illustrated in FIG. 6, external absorbent device 30, also described with respect to FIG. 3, but shown in FIG. 6 without wings 46*a* and 46*b* and strings 36*c* and 36*d*, includes an external tampon portion 32 resting on sanitary napkin portion 34 in the normal or home position. External tampon portion 32 is attached to sanitary napkin portion 34 by strings 36*a-d* and is shown in the "home" position in contact with and centrally located on sanitary napkin portion 34. From the home position, tampon portion 32 can move back and forth in each of two directions laterally and transversely of sanitary napkin portion 34 and vertically up (and then down) from sanitary napkin portion 34. A suitable adhesive located between outer layer 42' and pad 34' of sanitary napkin 34 can be used for this attachment. Sanitary napkin portion 34 includes wicking layer 138, a superabsorbent layer 140, and a non-permeable layer 142.

In another embodiment, the present invention is directed to a method of absorbing bodily fluids. An external absorbent device is provided. The external absorbent device comprises an external tampon portion that absorbs fluids and comprises a first end and a second end, wherein the external tampon portion is generally rod-shaped and comprises an outer surface to come into contact with a labia. The external absorbent device further comprises a sanitary napkin portion that absorbs fluids. The sanitary napkin portion is an elongate member comprising a first end, a second end, a first side, a second side, a top surface, and a bottom surface. The external tampon portion is movably affixed to the sanitary napkin portion.

The sanitary napkin portion of the external absorbent device is attached to the crotch portion of an undergarment. The external tampon portion of the external absorbent device is interlabially positioned by fitting the external tampon portion between the labia of a wearer.

A single string external absorbent device 150 is illustrated in FIGS. 9 and 10. External absorbent device 150 is similar to device 10, including a tampon portion 152 movably secured to a sanitary napkin portion 154 by string 156 that is centrally disposed within tampon portion 152 and adhesively attached between top layer 158 and bottom layer 160 of sanitary napkin portion 154. Sanitary napkin portion 154 is in the form of a thong panty liner, having a first end 162 and a second end 164 and sanitary napkin portion 154 gradually tapers from first end 162 to second end 164. First end 162 is wider than second end 164. Second end 164 is narrow enough to fit inside of a thong undergarment. Sanitary napkin portion 154 narrows along its longitudinal axis between first end 162 and second end 164, in a manner so as to permit placement inside of a thong undergarment without being exteriorly visible, thereby permitting use with thong bathing suits.

String 156 has sufficient slack to permit the desired amount of movement of tampon portion 152 relative to sanitary napkin portion 154, as described herein with respect to other embodiments of the invention. Slack in string 156 can be reduced to maintain tampon portion 152 above sanitary napkin portion 154, preventing tampon portion 152 from moving off of the edge of sanitary napkin portion 154. Alternatively, string 156 could be composed of two strings (not shown) for example by the central portion 156' of string 156, located within tampon portion 152, being omitted. External tampon portion 152 can be attached to sanitary napkin portion 154 using any method of attachment described herein. Additionally, use of a single string instead of a plurality of strings can be used in any of the external tampons described herein.

EXAMPLES

The present invention is described in more detail with reference to the following non-limiting examples, which are offered to more fully illustrate the invention, but are not to be construed as limiting the scope thereof.

Example 1

An external absorbent device is provided. The external absorbent device has an external tampon portion, a sanitary napkin portion, and four strings movably affixing the external tampon portion to the sanitary napkin portion. The external tampon portion moves with respect to the sanitary napkin portion, thus allowing for proper positioning within an individual wearer's labia. The proper interlabial positioning promotes enhanced absorbency of the external tampon portion, increased comfort to the wearer, and reduced leakage of any bodily fluids.

While the invention has been described with respect to certain preferred embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An external absorbent device comprising:
an elongated sanitary napkin portion that absorbs fluids; and
an external tampon portion that is fluid absorbent, the external tampon portion having a body comprising fluid-absorbent material, the external tampon portion having an outer surface to come into contact with a labia, and the external tampon portion being movably secured to the sanitary napkin portion to allow movement of the entire external tampon portion relative to and away from the sanitary napkin portion while the sanitary napkin portion is flat and while the external tampon portion is secured to the sanitary napkin portion.

2. The external absorbent device of claim 1 wherein the external tampon portion is secured to the sanitary napkin portion to permit movement of the external tampon portion vertically, laterally and longitudinally relative to the sanitary napkin portion.

3. The external absorbent device of claim 1 wherein the external tampon portion comprises a mass of compressed fibers.

4. The external absorbent device of claim 1 wherein the external tampon portion comprises a superabsorbent material.

5. The external absorbent device of claim 1 wherein the external tampon portion is movably secured to the sanitary napkin portion with at least one elongated member attaching the external tampon portion to the sanitary napkin portion, the elongated member having sufficient slack to permit the movement of the external tampon portion away from the sanitary napkin portion.

6. The external absorbent device of claim 5 wherein the elongated member is adhesively secured to the sanitary napkin portion.

7. The external absorbent device of claim 5 wherein the elongated member is elastic.

8. The external absorbent device of claim 5 wherein the external tampon portion is configured to be placed between two labia of a human wearer.

9. The external absorbent device of claim 1 wherein the sanitary napkin portion comprises a superabsorbent material.

10. The external absorbent device of claim 1 wherein the sanitary napkin portion comprises a topsheet and an absorbent core.

11. The external absorbent device of claim 10 wherein the absorbent core comprises a fibrous web that can absorb fluids.

12. The external absorbent device of claim 1 wherein a bottom surface of the sanitary napkin portion comprises an adhesive material.

13. The external absorbent device of claim 1 further comprising a first string comprising a first end and a second end, a second string comprising a first end and a second end, a third string comprising a first end and a second end, and a fourth string comprising a first end and a second end, wherein the four strings affix the external tampon portion to the sanitary napkin portion.

14. The external absorbent device of claim 13,
wherein the first end of the first string is connected to a first end of the external tampon portion and the second end of the first string is connected to a first side of the sanitary napkin portion;
wherein the first end of the second string is connected to the first end of the external tampon portion and the second end of the second string is connected to a second side of the sanitary napkin portion;
wherein the first end of the third string is connected to a second end of the external tampon portion and the second end of the third string is connected to the first side of the sanitary napkin portion; and
wherein the first end of the fourth string is connected to the second end of the external tampon portion and the second end of the fourth string is connected to the second side of the sanitary napkin portion.

15. The external absorbent device of claim 14 wherein the first string and the second string are about the same length, and wherein the third string and the fourth string are about the same length.

16. The external absorbent device of claim 14 wherein the first string, the second string, the third string, and the fourth string are about the same length.

17. The external absorbent device of claim 14 wherein the external tampon portion is movably positionable between two labia.

18. The external absorbent device of claim 1 wherein the body is elongated and has two longitudinally-opposed ends that are both simultaneously movable relative to and away from the sanitary napkin portion while the external tampon portion is secured to the sanitary napkin portion.

19. A method of absorbing bodily fluids with an external absorbent device having an elongated sanitary napkin that absorbs fluids and an external tampon portion that is fluid absorbent and being movably secured to the sanitary napkin portion to allow movement of the external tampon portion relative to and away from the sanitary napkin portion while the sanitary napkin portion is flat and while the external tampon portion is secured to the sanitary napkin portion, the method comprising:
attaching the sanitary napkin portion to an undergarment, the sanitary napkin portion being fluid absorbent; and
interlabially positioning the external tampon portion.

20. The method of claim 19 further comprising the adjusting the positioning of the external tampon portion to a comfortable fit.

21. The method of claim 19 wherein the external absorbent device further comprises:
a first string, a second string, a third string, and a fourth string, wherein the four strings attach the external tampon portion to the sanitary napkin portion, and wherein the four strings are about the same length.

22. The method of claim 19 wherein the external tampon portion comprises a mass of compressed fibers comprising a superabsorbent material, and wherein the sanitary napkin portion comprises a topsheet and an absorbent core, wherein the absorbent core comprises a fibrous web that can absorb fluids.

23. The method of claim 22 further comprising:
after the external tampon portion is interlabially positioned, absorbing fluids in the external tampon portion; and
absorbing any spillover fluids in the sanitary napkin portion.

24. The method of claim 19 wherein the external tampon portion is movably secured to the sanitary napkin portion with at least one elongated member attaching the external tampon portion to the sanitary napkin portion, the elongated member having sufficient slack to permit the away movement of the external tampon portion.

25. The method of claim 19 wherein the external tampon portion is elongated and has two longitudinally-opposed ends that are both simultaneously movable relative to and away from the sanitary napkin portion while the external tampon portion is secured to the sanitary napkin portion.

* * * * *